(12) United States Patent
Kopelman

(10) Patent No.: US 11,779,444 B2
(45) Date of Patent: *Oct. 10, 2023

(54) METHODS AND SYSTEMS FOR DENTAL PROCEDURES

(71) Applicant: Align Technology, Inc., San Jose, CA (US)

(72) Inventor: Avi Kopelman, Palo Alto, CA (US)

(73) Assignee: Align Technology, Inc., San Jose, CA (US)

(*) Notice: Subject to any disclaimer, the term of this patent is extended or adjusted under 35 U.S.C. 154(b) by 111 days.

This patent is subject to a terminal disclaimer.

(21) Appl. No.: 17/322,729

(22) Filed: May 17, 2021

(65) Prior Publication Data

US 2021/0267729 A1 Sep. 2, 2021

Related U.S. Application Data

(60) Continuation of application No. 16/179,394, filed on Nov. 2, 2018, now Pat. No. 11,033,368, which is a continuation of application No. 15/493,822, filed on Apr. 21, 2017, now Pat. No. 10,188,490, which is a division of application No. 13/787,634, filed on Mar. 6, 2013, now Pat. No. 9,668,829.

(60) Provisional application No. 61/739,450, filed on Dec. 19, 2012.

(51) Int. Cl.
| | | |
|---|---|---|
| *A61C 9/00* | (2006.01) | |
| *A61C 7/00* | (2006.01) | |
| *A61C 19/045* | (2006.01) | |
| *A61C 19/04* | (2006.01) | |
| *A61C 13/00* | (2006.01) | |
| *A61B 90/90* | (2016.01) | |
| *A61B 1/00* | (2006.01) | |
| *A61B 1/24* | (2006.01) | |
| *G16H 20/40* | (2018.01) | |
| *A61B 90/00* | (2016.01) | |

(52) U.S. Cl.
CPC ........ *A61C 19/045* (2013.01); *A61B 1/00045* (2013.01); *A61B 1/000095* (2022.02); *A61B 1/24* (2013.01); *A61B 90/90* (2016.02); *A61C 7/002* (2013.01); *A61C 9/0053* (2013.01); *A61C 9/0066* (2013.01); *A61C 13/0004* (2013.01); *A61C 19/04* (2013.01); *A61B 2090/3937* (2016.02); *G16H 20/40* (2018.01)

(58) Field of Classification Search
CPC .............................. A61C 9/0066; A61B 90/90
See application file for complete search history.

(56) References Cited

U.S. PATENT DOCUMENTS

| | | |
|---|---|---|
| 6,334,772 B1 | 1/2002 | Taub et al. |
| 6,334,853 B1 | 1/2002 | Kopelman et al. |
| 6,463,344 B1 | 10/2002 | Pavlovskaia et al. |
| 6,542,249 B1 | 4/2003 | Kofman et al. |
| 6,633,789 B1 | 10/2003 | Nikolskiy et al. |
| 6,664,986 B1 | 12/2003 | Kopelman et al. |
| 6,697,164 B1 | 2/2004 | Babayoff et al. |
| 6,845,175 B2 | 1/2005 | Kopelman et al. |
| 6,979,196 B2 | 12/2005 | Nikolskiy et al. |
| 7,030,383 B2 | 4/2006 | Babayoff et al. |

(Continued)

*Primary Examiner* — Santiago Garcia
(74) *Attorney, Agent, or Firm* — Wilson Sonsini Goodrich & Rosati

(57) ABSTRACT

A device including a coded pattern for use in dental procedures is provided. Related methods and systems are also provided.

20 Claims, 10 Drawing Sheets

(56) References Cited

U.S. PATENT DOCUMENTS

| | | |
|---|---|---|
| 7,202,466 B2 | 4/2007 | Babayoff et al. |
| 7,255,558 B2 | 8/2007 | Babayoff et al. |
| 7,286,954 B2 | 10/2007 | Kopelman et al. |
| 7,373,286 B2 | 5/2008 | Nikolskiy et al. |
| 7,507,088 B2 | 3/2009 | Taub et al. |
| 7,545,372 B2 | 6/2009 | Kopelman et al. |
| 7,698,068 B2 | 4/2010 | Babayoff |
| 7,916,911 B2 | 3/2011 | Kaza et al. |
| 8,108,189 B2 | 1/2012 | Chelnokov et al. |
| 8,244,028 B2 | 8/2012 | Kuo et al. |
| 8,587,582 B2 | 11/2013 | Matov et al. |
| 8,948,482 B2 | 2/2015 | Levin |
| D742,518 S | 11/2015 | Barak et al. |
| 9,192,305 B2 | 11/2015 | Levin |
| 9,261,356 B2 | 2/2016 | Lampert et al. |
| 9,261,358 B2 | 2/2016 | Atiya et al. |
| 9,299,192 B2 | 3/2016 | Kopelman |
| D760,901 S | 7/2016 | Barak et al. |
| 9,393,087 B2 | 7/2016 | Moalem |
| 9,431,887 B2 | 8/2016 | Boltanski |
| 9,439,568 B2 | 9/2016 | Atiya et al. |
| 9,451,873 B1 | 9/2016 | Kopelman et al. |
| D768,861 S | 10/2016 | Barak et al. |
| D771,817 S | 11/2016 | Barak et al. |
| 9,491,863 B2 | 11/2016 | Boltanski |
| D774,193 S | 12/2016 | Makmel et al. |
| 9,510,757 B2 | 12/2016 | Kopelman et al. |
| 9,660,418 B2 | 5/2017 | Atiya et al. |
| 9,668,829 B2 * | 6/2017 | Kopelman ............. A61B 90/90 |
| 9,675,430 B2 | 6/2017 | Verker et al. |
| 9,693,839 B2 | 7/2017 | Atiya et al. |
| 9,717,402 B2 | 8/2017 | Lampert et al. |
| 9,724,177 B2 | 8/2017 | Levin |
| 9,844,426 B2 | 12/2017 | Atiya et al. |
| 9,907,626 B1 * | 3/2018 | Lowe ..................... A61C 7/008 |
| 10,076,389 B2 | 9/2018 | Wu et al. |
| 10,108,269 B2 | 10/2018 | Sabina et al. |
| 10,111,581 B2 | 10/2018 | Makmel |
| 10,111,714 B2 | 10/2018 | Kopelman et al. |
| 10,123,706 B2 | 11/2018 | Elbaz et al. |
| 10,136,972 B2 | 11/2018 | Sabina et al. |
| 10,188,490 B2 * | 1/2019 | Kopelman ............. A61C 19/04 |
| 10,380,212 B2 | 8/2019 | Elbaz et al. |
| 10,390,913 B2 | 8/2019 | Sabina et al. |
| 10,453,269 B2 | 10/2019 | Furst |
| 10,456,043 B2 | 10/2019 | Atiya et al. |
| 10,499,793 B2 | 12/2019 | Ozerov et al. |
| 10,504,386 B2 | 12/2019 | Levin et al. |
| 10,507,087 B2 | 12/2019 | Elbaz et al. |
| 10,517,482 B2 | 12/2019 | Sato et al. |
| 10,695,150 B2 | 6/2020 | Kopelman et al. |
| 10,708,574 B2 | 7/2020 | Furst et al. |
| 10,744,196 B2 * | 8/2020 | Vujadinovic ......... C07K 14/005 |
| 10,772,506 B2 | 9/2020 | Atiya et al. |
| 10,813,727 B2 | 10/2020 | Sabina et al. |
| 10,888,399 B2 | 1/2021 | Kopelman et al. |
| 10,952,816 B2 | 3/2021 | Kopelman |
| 10,980,613 B2 | 4/2021 | Shanjani et al. |
| 11,013,581 B2 | 5/2021 | Sabina et al. |
| 11,033,368 B2 * | 6/2021 | Kopelman ......... A61B 1/00045 |
| D925,739 S | 7/2021 | Shalev et al. |
| 11,096,765 B2 | 8/2021 | Atiya et al. |
| 11,238,586 B2 | 2/2022 | Minchenkov et al. |
| 2006/0154198 A1 * | 7/2006 | Durbin ..................... G06T 17/00 433/29 |
| 2010/0191510 A1 * | 7/2010 | Kopelman ........... A61C 19/045 703/1 |
| 2013/0218531 A1 * | 8/2013 | Deichmann ............... A61C 5/77 703/1 |
| 2015/0079533 A1 * | 3/2015 | Lowe ..................... G16H 20/40 433/24 |
| 2016/0361140 A1 * | 12/2016 | Lowe ..................... A61C 7/002 |
| 2019/0029784 A1 | 1/2019 | Moalem et al. |
| 2019/0388193 A1 | 12/2019 | Saphier et al. |
| 2020/0281700 A1 | 9/2020 | Kopelman et al. |
| 2020/0281702 A1 | 9/2020 | Kopelman et al. |
| 2020/0315434 A1 | 10/2020 | Kopelman et al. |
| 2020/0349705 A1 | 11/2020 | Minchenkov et al. |
| 2020/0404243 A1 | 12/2020 | Saphier et al. |
| 2021/0030503 A1 | 2/2021 | Shalev et al. |
| 2021/0059796 A1 | 3/2021 | Weiss et al. |
| 2021/0068773 A1 | 3/2021 | Moshe et al. |
| 2021/0121049 A1 | 4/2021 | Rudnitsky et al. |
| 2021/0128281 A1 | 5/2021 | Peleg |
| 2021/0137653 A1 | 5/2021 | Saphier et al. |
| 2021/0196152 A1 | 7/2021 | Saphier et al. |

* cited by examiner

FIG. 8A — Coded grid that will provide the orientation between the captured area to the vertical and horizontal references.

Flap pushes the upper lip to expose the teeth for scanning

METHODS AND SYSTEMS FOR DENTAL PROCEDURES

CROSS-REFERENCE

This application is a continuation application of U.S. application Ser. No. 16/179,394, filed Nov. 2, 2018, now U.S. Pat. No. 11,033,368, issued Jun. 15, 2021, which is a continuation application of U.S. application Ser. No. 15/493,822, filed Apr. 21, 2017, now U.S. Pat. No. 10,188,490, issued Jan. 29, 2019, which is a divisional application of U.S. application Ser. No. 13/787,634, filed Mar. 6, 2013, now U.S. Pat. No. 9,668,829, issued Jun. 6, 2017, which claims the benefit of U.S. Provisional Application No. 61/739,450, filed Dec. 19, 2012, each of which are incorporated herein by reference in their entirety.

BACKGROUND OF THE INVENTION

Articulators are well known dental devices which attempt to replicate the movement of the lower jaw relative to the upper jaw about the Temporomandibular Joint (TMJ) in a patient-specific manner. Plaster models of the patient's upper and lower teeth arches can be mounted to the articulator with respect to its hinge axis in a manner simulating that of the real teeth arches with respect to the patient's TMJ joint. Traditionally, physical impressions of the dental arches are provided, which are then used for casting the plaster models. In addition, a bite impression is obtained with a wax bite plate, which records the relative positions of the upper and lower arches.

A mechanical facebow with a bite fork can be used for obtaining patient-specific measurements which are then used to set up the plaster model in a particular articulator. In particular, the spatial orientation of the patient's maxillary arch with respect to the ear canals is duplicated by the facebow. The facebow is engaged to the ear canals via an ear canal insertion portion. Then, a bite fork with impression material is brought into engagement with the maxillary teeth, and a jig connects the bite fork via its arm to the facebow. The facebow and bite fork combination are then mechanically rigidly coupled to the articulator, such that the ear canal insertion portions are in the corresponding alignment with the pivot axis of the articulator. The plaster models are mounted to the articulator so as to engage and thus match the position of the bite fork, and plaster filling is provided between each plaster model and the respective articulator arm. This is a complicated and time consuming process, and which requires expert handling.

While facebows can be used to facilitate determining the patient-specific measurements needed to accurately place physical models of the patient's teeth into an articulator, there is a need for additional advancements. For example, methods, devices and systems are needed that can increase the speed of acquiring the patient specific measurements during a visit to a dental practitioner and/or provide more accurate measurements for use in mounting physical models to an articulator.

SUMMARY OF THE INVENTION

The present invention provides systems, methods and devices having a coded pattern for use in dental procedures. In an example, the present invention provides a device including a coded pattern that can, e.g., be used to improve scanning time and accuracy for generating digital data using in dental procedures.

In some aspects, the present invention provides a device for use in dental scanning procedures of a patient. The device can include an occlusal portion and a non-occlusal portion, the occlusal portion comprising a bite plate for securing the device positioned in a patient's mouth during a scanning procedure and the non-occlusal portion comprising a coded pattern for aligning scanned images of the patient, the occlusal portion and the non-occlusal portion being coupled together at an angle such that the coded pattern is outwardly oriented from the patient's mouth when the bite plate is positioned between the patient's teeth, so that the coded pattern is presented to permit scanning of the coded pattern simultaneously when scanning at least some of the patient's teeth. Related methods and systems are also provided.

For a fuller understanding of the nature and advantages of the present invention, reference should be made to the ensuing detailed description and accompanying drawings. Other aspects, objects and advantages of the invention will be apparent from the drawings and detailed description that follows.

BRIEF DESCRIPTION OF THE DRAWINGS

FIG. 4A shows positioning of a device in front of a patient's face. FIG. 4B shows aligning the device with a patient's sagittal plane. FIG. 4C shows scanning the coded pattern of the device and at least a portion of the patient's teeth.

FIG. 8A illustrates a head-on view of a patient in relation to a device having a coded pattern and FIG. 8B illustrates a profile view of the device having a lip displacement attachment, in accordance with an embodiment of the present invention.

DETAILED DESCRIPTION OF THE INVENTION

Figure 1:
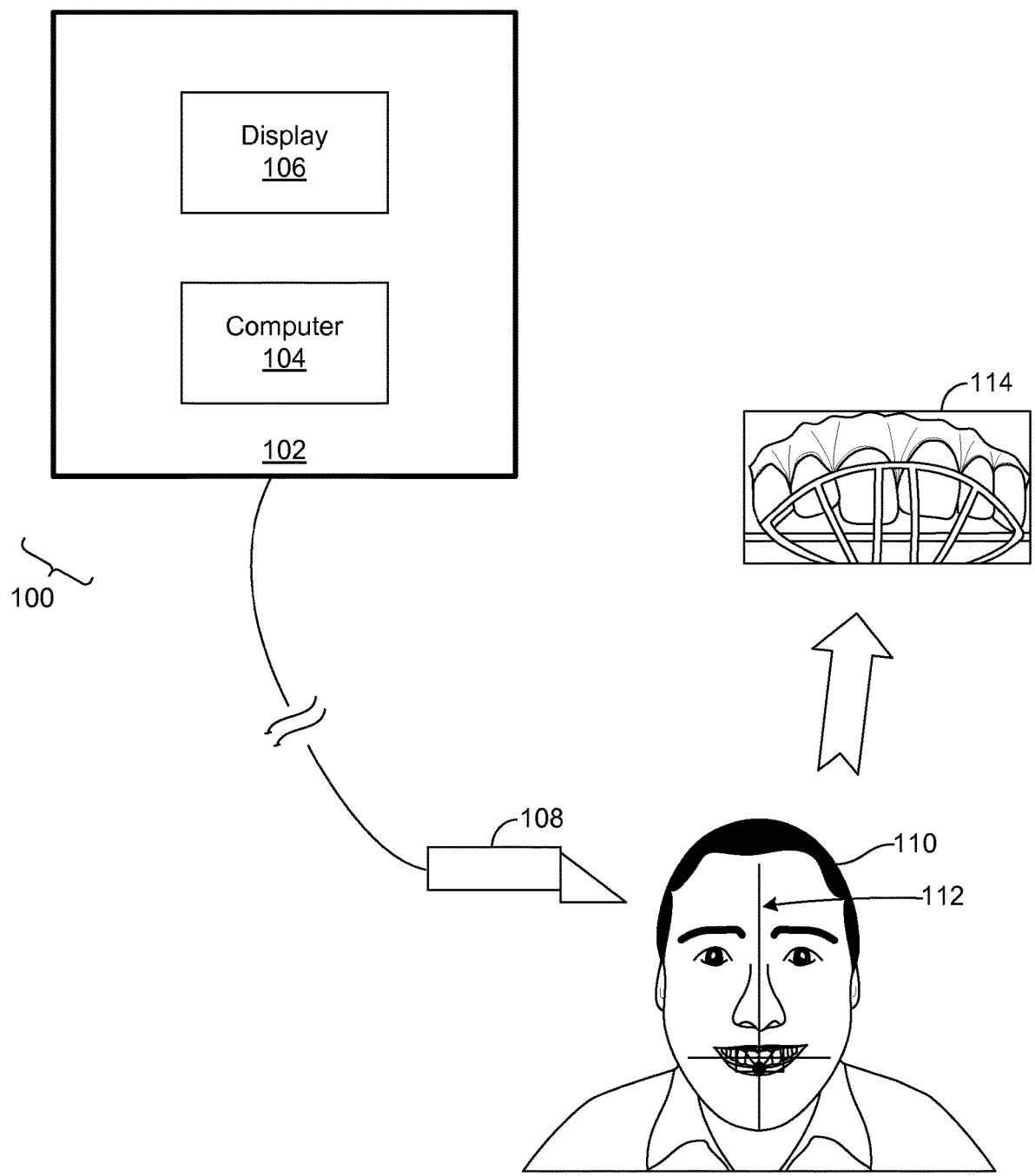
FIG. 1 depicts a system including a device having a coded pattern, in accordance with an embodiment of the present invention.

The present invention provides a device having a coded pattern for use in dental procedures. In an example, the present invention provides a device including a coded pattern that can, e.g., be used to improve scanning time and accuracy for generating digital data using in dental procedures. Related methods and systems are also provided.

As will be described herein, one aspect of the present invention includes using the devices described herein to generate physical models of a patient's teeth for mounting in an articulator and in an arrangement that accurately represents the relative positions of all or a portion of a patient's upper and lower arch. Accurate representations of positions of the patient's teeth can be facilitated by determining a spatial relationship between the patient's teeth and a reference, e.g., a reference point on the patient, such as the sagittal plane of the patient's face. In some aspects, the present invention provides devices having a coded pattern that improves capabilities for quickly and accurately determining spatial relationships that are used to produce accurate placement of physical models in an articulator. As will be described herein, the coded pattern, for example, can be designed to allow for easier and more efficient alignment of scan images taken of the patient and the device having the coded pattern.

The present invention includes scanning systems that can be used for a variety of procedures, such as scanning a patient's teeth, scanning devices worn by a patient, and/or scanning a patient wearing a device having a coded pattern. In one aspect, the present invention includes a system for digitally aligning a patient's teeth with a reference portion of the patient. The system can include a device comprising an occlusal portion and a non-occlusal portion, the occlusal portion comprising a bite plate for securing the device positioned in a patient's mouth during a scanning procedure and the non-occlusal portion comprising a coded pattern for aligning scanned images of the patient, the occlusal portion and the non-occlusal portion being coupled together at an angle such that the coded pattern is outwardly oriented from the patient's mouth when the bite plate is positioned between the patient's teeth, so that the coded pattern is presented to permit scanning of the coded pattern simultaneously when scanning at least a portion of the patient's teeth, the device further comprising at least one extension portion capable of being aligned with the reference portion. The system can also include a scanner for acquiring a first image of at least the portion of the patient's teeth and a second image of the coded pattern and at least the portion of the patient's teeth; and a computer comprising storage media comprising instructions that, when executed, cause the computer to determine a spatial relationship between at least some of the patient's teeth and the reference portion associated with the patient by calculating a first spatial relationship between the device and at least the portion of the patient's teeth and a second spatial relationship between the device and the reference portion.

Referring to FIG. 1, a scanning system 100 of the present invention can include a computer system 102 having a computer 104 and a display 106. The system 100 can also include a scanner 108 that can be used to scan a patient 110 and a device having a coded pattern 112. The scans can be used, e.g., to generate three dimensional (3D) digital models 114 of the coded pattern and at least a portion of the patient's teeth. The computer system 100 can include a microprocessor, memory, or any other suitable hardware configured to process a scanned image of the patient and the device having the coded pattern. The computer system 100 can also include input modules such as a keyboard, mouse, tablet, and so on. The display 106 (or output device) can include a screen or monitor but may also include a printer, or any other display system. The display of the system, e.g., can be used to show the generated 3D digital models (e.g., of the coded pattern).

A variety of scanners can be used in the present invention, e.g., to acquire scan images of a device having a coded pattern in relation to a patient's teeth. The scanner 108, for example, can be configured to acquire surface topology of structures, in particular dental surfaces of dental structures and/or other tissue surfaces of the face and head of a patient. In one embodiment, the scanner 108 can be used to acquire scan image data for 3D digital models 114 of the device having the coded pattern along with at least a portion of the patient's teeth. As shown in FIG. 1, the scanner 108 is also operatively connected to the computer system 102. The computing system 102 is suitably programmed for reconstructing scanned surfaces from the surface data provided, to provide a corresponding digital model of the structure scanned by the scanner. The scanner 108 may also include, for example, any suitable non-contact scanner, for example an optical scanner. By way of non-limiting example, the scanner 108 may include a probe for determining a three dimensional (3D) structure by confocal focusing of an array of light beams, for example, as disclosed in WO 00/08415, the contents of which are incorporated herein in their entirety. Alternatively, the required scanning may be accomplished using any other suitable scanning apparatus, for example comprising a hand-held probe.

In some embodiments, the present invention includes acquiring color image data of the intraoral cavity that can be provided together with the scan image data to provide a digital model that includes 3D digital data representing the surfaces of the structures as well as color information of the structures scanned, such as for example of dental surfaces. Examples of such scanners are disclosed in, for example, US 2006/0001739, which is incorporated herein by reference in its entirety.

The scanning systems of the present invention can also be used for generating 3D digital models of all or a portion of an intraoral cavity. In some embodiments, the system can also be configured to scan and generate 3D digital models of the upper and/or lower arch of the patient. In certain embodiments, the system can be configured to scan and generate 3D digital models of the upper and lower arches together in occlusion. As described further herein, the 3D digital models can be used for certain aspects of the methods of the present invention. For example, the 3D digital models can be used in alignment procedures and/or for generating physical models that accurately represent actual positions of the patient's teeth when the models are mounted in an articulator. The 3D digital models can include topographical data representing a variety of dental structures such as one or more teeth, partial or the full mandibular or maxillary arches, or both arches, and/or details of the spatial relationship between the upper and lower arches in occlusion as well as surrounding tissue, such as gums, and other dental prosthetics (e.g., crowns).

The 3D digital models can be acquired using a variety of suitable methods. In one embodiment, 3D digital models can be obtained by scanning a patient's intraoral cavity using any suitable equipment for scanning a patient's teeth. Such scanning equipment may include any suitable optical scanner, for example, the scanner 108 of system 100, a similar scanner that is not part of the system 100, or a different type of scanner. In alternative embodiment, the 3D digital models can be obtained from a physical model of the teeth of the particular patient. For example, the surfaces of the physical model can be scanned, or the surfaces of the impression from which the model was scanned can be scanned to obtain the digital model. In some embodiments, scans can be taken of physical models of a patient's lower arch, upper arch, and the arches in occlusion. Together with a scan of the coded pattern at least a portion of the patient's teeth, the physical models can then be modified, e.g., with alignment structures that provide for accurate representation of the patient's occlusion when the models are mounted in an articulator (e.g. holes in the models can have predetermined shapes, sizes and/or orientations for accurate mounting in an articulator). In some embodiments, a composite positive-negative model can be manufactured and processed to obtain 3D digitized data, for example as disclosed in U.S. Pat. No. 6,099,314, the content of which is incorporated herein in its entirety. Alternatively, the 3D digitized data may be obtained in any other suitable manner, including other suitable intra oral scanning techniques, based on optical methods, direct contact methods or any other means, applied directly to the patient's dentition or to a physical model thereof. X-ray based, CT based, MM based, or any other type of scanning of the patient or of a positive and/or negative physical model of the intra-oral cavity can be used, as well. 3D digital models can also be obtained by other ways, such as from an electronic record or another practitioner or scanning facility.

The present invention further includes methods for scanning a patient's teeth to determine a spatial relationship between the teeth and a reference. In one aspect, the present invention includes a method for digitally aligning a patient's teeth with a reference portion of the patient. The method can include acquiring, using a scanner, a first image of at least a portion of the patient's teeth. The method can also include positioning a device in a patient's mouth to align the device with a reference portion of the patient, the device comprising an occlusal portion and a non-occlusal portion, the occlusal portion comprising a bite plate held between the patient's teeth so as to secure the device in a position during a scanning procedure and the non-occlusal portion comprising a coded pattern for aligning scanned images of the patient, the occlusal portion and the non-occlusal portion being coupled together at an angle such that the coded pattern is outwardly oriented from the patient's mouth when the bite plate is positioned between the patient's teeth, so that the coded pattern is presented to permit scanning of the coded pattern simultaneously when scanning at least the portion of the patient's teeth. The methods can include acquiring, using the scanner, a second image of at least a portion of the coded pattern and at least the portion of the patient's teeth; and processing the first image and the second image to determine a spatial relationship between at least the portion of the patient's teeth and the reference portion by calculating a first spatial relationship between at least the portion of the coded pattern and at least the portion of the patient's teeth and the alignment between the device and the reference portion.

Figure 2:
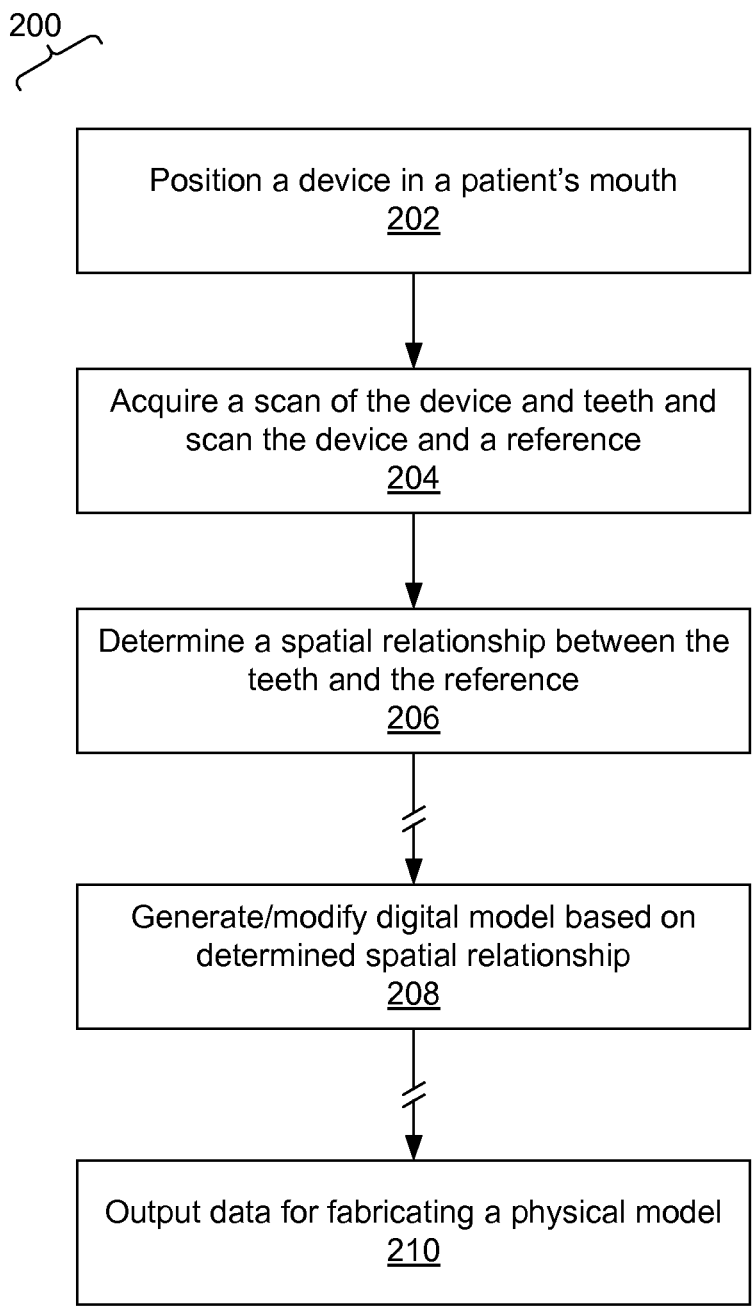
FIG. 2 shows an example method for determining a spatial relationship between a patient's teeth and a reference, in accordance with an embodiment of the present invention.

FIG. 2 shows an example method 200 of the present invention. In Step 202, a device disclosed herein is positioned in a patient's mouth. In Step 204, a scan is acquired of the device and the teeth. A scan of the device and a reference is also acquired. In Step 206, the method includes determining a spatial relationship between the teeth and the reference. In some embodiments, the methods can further include Step 208, generating and/or modifying 3D digital models of the patient's teeth based on the determined spatial relationship between the teeth and the reference. In certain embodiments, the method can also include Step 210, outputting and/or using the 3D digital models and the determined spatial relationship data to fabricate physical models of the patient's teeth.

Figure 3:
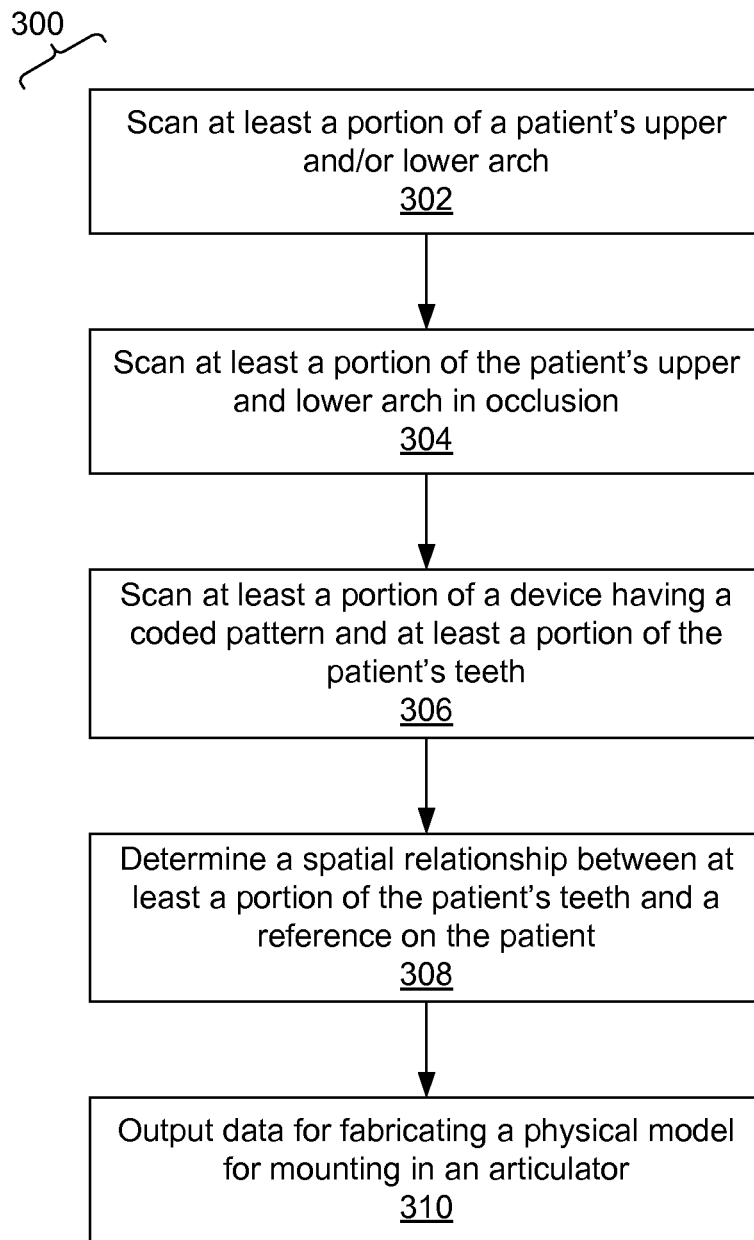
FIG. 3 shows an example method for determining a spatial relationship between a patient's teeth and a reference, in accordance with an embodiment of the present invention.

FIG. 3 shows another example method 300 of the present invention. In Step 302, a scan can be acquired of at least a portion of the patient's upper and/or lower arches. In some embodiments, a full scan of the upper and lower arch can be acquired and used for fabricating physical models. The arches can include regions for installing a prosthodontic dental appliance, e.g., a crown and/or a bridge. In Step 304, a scan can be acquired of at least a portion of the patient's upper and/or lower arches in occlusion. Scan image data acquired at this step can be used, e.g., for determining how to fabricate the physical models such that they can be mounted in an articulator in proper occlusion, e.g., without any additional manipulation of the models to achieve accurate and proper patient occlusion. In Step 306, a scan can be acquired of a device having a coded pattern and at least a portion of the patient's teeth. In some embodiments, the device can also include extension portions or other structures that can align with a reference (e.g., a facial feature on the patient, such as the sagittal plane). A scan of the device can also include scanning the extension portion. In Step 308, a spatial relationship between at least a portion of the patient's teeth and the reference can be determined. For example, the scan image data of the upper and lower arch in occlusion can be matched with the scan image data of the device and at least a portion of the patient's teeth to determine how the patient's occlusion is spatially oriented in relation to the reference, e.g., the sagittal plane. Alternatively, the scan image data of the device and at least a portion of the patient's teeth can be compared (e.g., matched) with other scan image data acquired of the patient's upper and/or lower arches. Based on these steps, data can be produced that can be output to a fabrication machine for fabricating physical models of the patient's teeth. In some embodiments, the physical models can include alignment structures (e.g., holes for mounting on an articulator) that have a location, shape, size and orientation on the physical model so as to place the upper and lower arch in proper and accurate occlusion upon mounting to the articulator. In certain embodiments, the method can also include Step 310, outputting and/or using the 3D digital models and the determined spatial relationship data to fabricate physical models of the patient's teeth.

In addition to other methods described herein, the determination of spatial relationships can be conducted in a variety of ways. In one aspect of the present invention, scan image data can be acquired to facilitate determination of a spatial relationship between a reference and a device having a coded pattern. For example, a spatial relationship between all or a portion of a patient's maxillary arch and a hinge axis of the jaw of a patient can be determined and then used for constructing physical models of the tooth arches that engage with a dental articulator in a spatial relationship with the articulator hinge axis that parallels the corresponding relationship in the patient.

In some embodiments, an accurate representation of a spatial relationship between a patient's arch and the jaw hinge axis can be determined, for example, by scanning at least one zone that can separately include all or a portion of a device having a coded pattern, at least one of the patient's teeth, and, in some embodiments, a reference, e.g., a reference of the patient. The number of zones scanned can depend on various factors, such as the desired accuracy and/or time considerations. In some instances, scanning of more zones may improve accuracy with a possible tradeoff of increased processing times.

In certain embodiments, one zone can be scanned and used to determine a spatial relationship that can be used to, e.g., produce physical models for mounting in an articulator, accurately representing a patient's occlusion. In one example, a scan zone can include at least a portion of a coded pattern and at least a portion of the patient's teeth (e.g., several teeth). As described further herein, the coded pattern can include structures and/or registration marks that allow determination of what part of the coded pattern is scanned. Data stored on the system or provided from elsewhere can be used to then identify where the scanned zone is in relation to a reference of the patient. In some embodiments, for example, the reference of the patient can be the sagittal plane of the patient. In such an embodiment, the device including the coded pattern can also include an extension portion that aligns with the patient's sagittal plane. Other facial features of the patient can also be used for alignment and scanning. For example, the device can also include a horizontal extension portion that is orthogonal to the patient's sagittal plane. Other facial features can include, for example, the TMJ, a mark placed on the patient's face, the patient's chin, nose, and/or eyes.

Figure 4A:
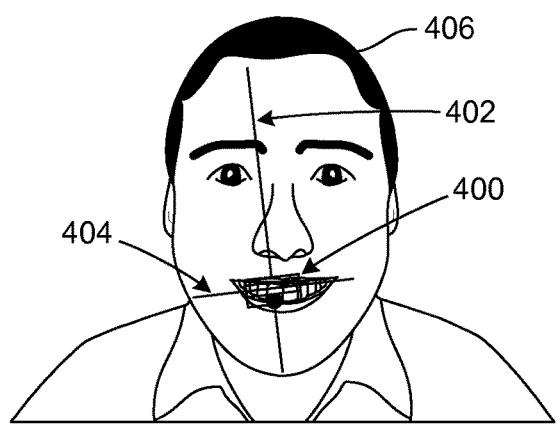
FIGS. 4A-C depicts steps in a method for determining a spatial relationship between a patient's teeth and a reference, in accordance with an embodiment of the present invention.
Figure 4B:
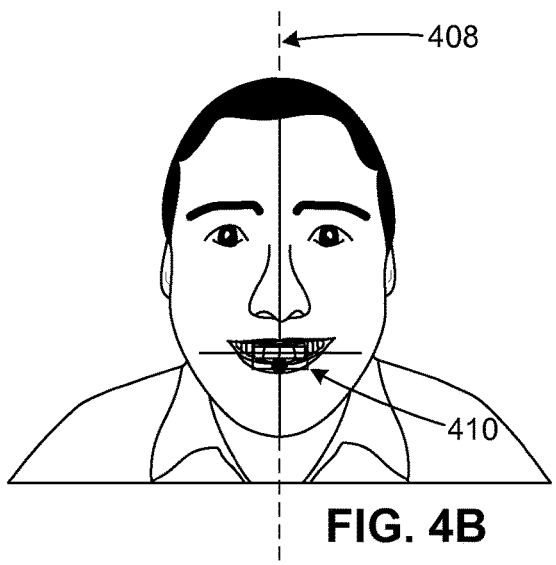
Figure 4C:
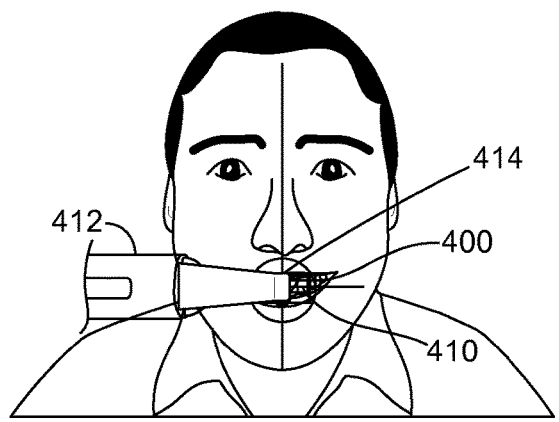

FIGS. 4A-4C provides an example embodiment using a scan of one zone to determine how a patient's upper and/or lower arch are positioned in space compared to a reference on the patient, e.g., the sagittal plane. As shown in FIG. 4A, a device having a coded pattern 400 and vertical 402 and horizontal 404 extension portions can be positioned in relation to a patient's face 406. FIG. 4B illustrates alignment of the device with the patient's sagittal plane 408 and positioning the coded pattern in front of the patient's teeth 410. FIG. 4C depicts a scanner 412 for scanning one zone including the coded pattern of the device 400 along with at least a portion of the patient's teeth 410. As described further herein, the scan image data acquired from the scan can be used for a variety of purposes, such as fabricating physical models of the patient's teeth for mounting in an articulator.

Figure 5:
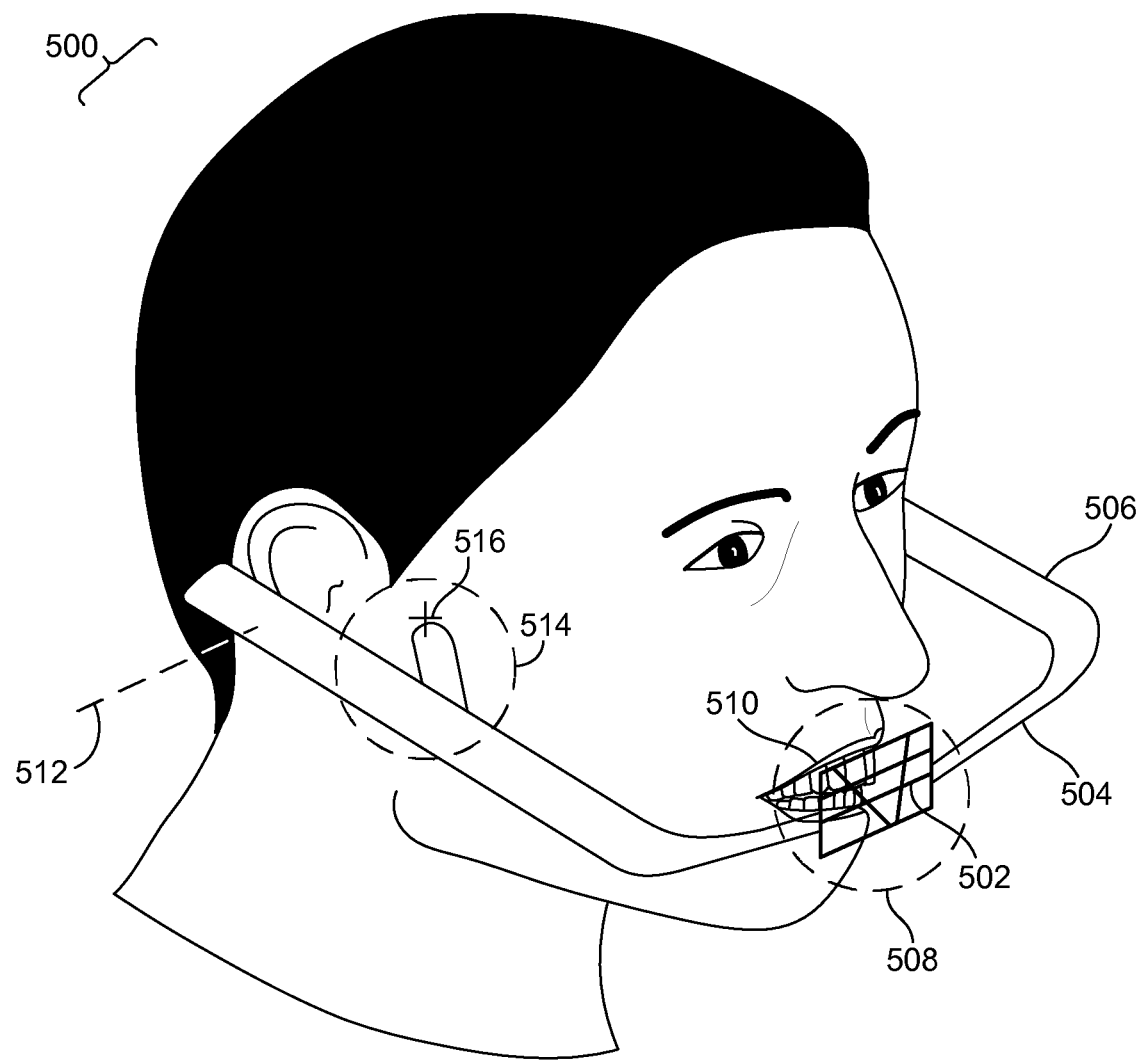
FIG. 5 illustrates a patient wearing a device including a coded pattern, in accordance with an embodiment of the present invention.

In some embodiments, two zones can be scanned and used to determine a spatial relationship. Alternatively, three or more zones can be scanned. FIG. 5 provides a representation of a scanning procedure 500 used to determine a spatial relationship between at least some of the patient's teeth and the patient's TMJ. As shown, a nonocclusal portion including a coded pattern 502 can be presented to permit scanning of the coded pattern simultaneously when scanning at least some of the patient's teeth. The coded pattern 502 can also be integrated with an extension portion 504 integrated with a facebow structure 506 as well as an occlusal portion of the device (not shown), which can be placed in the patient's mouth. The spatial orientation of the occlusal portion and the nonocclusal portion including the coded pattern can be fixed such that the device is rigidly held in relation to the patient during scanning. In an example sequence, Zone 1 (508) can be scanned using a scanner to acquire scan image data of at least some of the patient's teeth, at least a portion of the coded pattern and an extension portion 504 of the facebow structure 506. A digital model of Zone 1 can be generated and can include at least some of the patient's teeth 510, at least a portion of the coded pattern 502, and/or the extension portion 504. The relative position of a reference point on the patient, e.g., the ear canal axis 512 with respect to the extension portion 504 is known. Thus, the digital model of the patient's teeth 510, the coded pattern 502 and the extrusion portion 504 can then be registered with the position and orientation of the ear canal axis 512, which is a body reference of interest. The ear canal axis can be represented digitally, as well, and then be positioned with respect to the digital model of the patient's teeth in a common coordinate system.

In an alternative embodiment, another scan may be acquired of a Zone 2 (514) including markers 516, such that the position and orientation of the markers with respect to the extension portion 504 may be determined. In this instance, the position and orientation of the patient's TMJ, which can also be a reference point of interest, can be determined with respect to the digital model of the patient's teeth in a common coordinate system. In addition to the ear canal axis and the TMJ, there are several other possible reference points can be used for determining spatial relationships. For example, other reference points include, but are not limited to, the sagittal plane of the patient, an anatomical feature on the patient, or a marked feature on the patient (e.g., an inked marking).

In yet another embodiment, two zones can be scanned and used to determine the spatial relationship between at least some of the patient's teeth and a reference, e.g., an ear canal axis of the patient. In an example sequence, a first zone can be scanned using a scanner to acquire scan image data of at least some of the patient's teeth and at least a portion of the coded pattern. A digital model of the first zone can be generated and can include at least some of the patient's teeth and at least a portion of the coded pattern. A second zone can be scanned, which includes a portion of the coded pattern and a section of an extension portion. Zone 2 also includes a portion of an extension portion that is aligned or otherwise spatially oriented with a reference point of the patient. A digital model of the second zone can be generated and can include at least a portion of the coded pattern and the extension portion. Since the geometry of the coded pattern and the device is known, it is then possible to place the digital models of the first zone and the second zone in the same coordinate system. For example, the portion of the coded pattern that is scanned in the first zone and the second zone can be aligned digitally. The relative position of a reference point on the patient, e.g., the ear canal axis with respect to the extension portion is also known. Thus, the digital model of the patient's teeth including the coded pattern can then be registered with respect to a reference, e.g., the ear canal axis. The position and orientation of the ear canal can be determined with respect to the digital model of the patient's teeth in a common coordinate system.

The spatial relationship between at least a portion of the patient's teeth and a reference on the patient (e.g., the sagittal plane of the patient) can be determined by several different methods. For example, software modules can be used on the system to process scan image data so as to calculate dimensions and orientations of, e.g., the patient's upper and/or lower arch, the device having a coded pattern and/or extension portion, and the reference on the patient. In some embodiments, determination of the spatial relationship among various components can be performed digitally. For example, scan image data can include 3D digital models of the device having the coded pattern and an extension portion that has been acquired in alignment with a reference of the patient (e.g., the sagittal plane of the patient). The 3D digital model can further include scan image data of at least a portion of the patient's teeth. Additional 3D digital models can also be provided of the patient's upper arch and/or the lower arch, as well as the patient's upper and lower arches in occlusion. In some embodiments, the 3D digital models of the patient's upper and/or lower arches can be visually aligned with the 3D digital model of the device having the coded pattern and at least a portion of the patient's teeth. For instance, the 3D digital model of the coded pattern can include at least a portion of the patient's incisors and canines in the upper arch. These teeth can then be visually overlaid with the same corresponding teeth in the 3D digital model of the patient's upper arch scan data. Alternatively, matching algorithms or other ways to overlay the digital models can be used for alignment. Given that the coded pattern data was obtained in alignment with, e.g., the sagittal plane of the patient, the scan image data of the upper arch can then be aligned with the sagittal plane. This alignment information can be used to generate a physical model in a digital form that can be used to ultimately make a physical model in a physical form. In some embodiments, the physical models in digital form can be mounted on an articulator that is also in digital form. In such an embodiment, alignment structures (e.g., mounting holes or other markings) can be added to the digital physical model such that the physical models (e.g., of the upper and lower arch) mount on the articulator and fit together in proper occlusion according to the particular patient. The spatial relationship data determined using the methods and systems herein can also be used to make physical models that can be placed in proper occlusion using ways other than mounting in an articulator. For example, the physical models can be fabricated to include alignment structures that can, e.g., clip the upper and lower arches together, or portions thereof, in proper occlusion corresponding to the patient's actual occlusion.

Figure 6A:
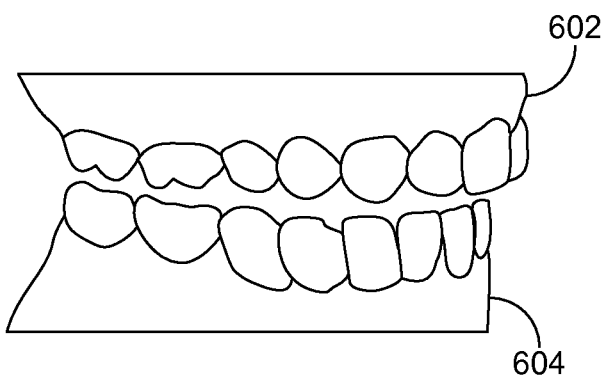
FIG. 6A shows a front view of physical models of a lower and upper arch of a patient's teeth.
Figure 6B:
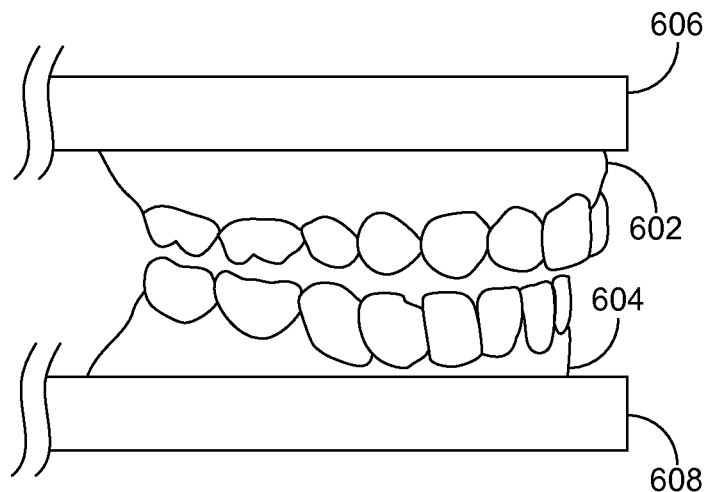
FIG. 6B shows the physical models each mounted on a respective base and couplable to an articulator, in accordance with an embodiment of the present invention.

The accurate information acquired for the spatial relationship of the patient's teeth and a reference can be used in a variety of dental procedures. For example, with a known spatial relationship between at least some of the patient's teeth and a reference point on the patient (e.g., the sagittal plane), physical models of the patient's teeth can be positioned within an articulator in an accurate orientation that is consistent with the patient's actual orientation. There are several suitable avenues for accurately positioning one or both physical arch models in an articulator. FIG. 6A shows a front view of two physical arch models representing a patient's upper arch 602 and lower arch 604. FIG. 6B shows the two physical arch models 602, 604 of the patient's teeth each mounted on a top base 606 and a bottom base 608 that, for example, can be coupled to an articulator so as to position the physical models in a relative orientation, e.g., in proper occlusion that represents the patient's occlusion. Using the determined spatial relationship between at least some of the patient's teeth and a reference point on the patient, a technician or other dental practitioner can accurately mount the physical models in the articulator. In some embodiments, the base of the physical model can be molded or fabricated so as to have a particular structure that orients the physical model in the correct position when it is placed in the articulator. Alternatively, the components of the articulator can be positioned in a manner so as to place a physical model in the correct position. In one aspect, the present invention includes a physical model having a structure that when mounted in an articulator correctly represents the actual orientation of the patient's arch. In addition, the upper and lower arches can be manufactured to accurately represent the relative positions of the teeth in each arch in occlusion, e.g., an occlusal spatial relationship. It is also noted that in addition to designing the physical models for mounting in an articulator, the present invention further includes providing data for fabricating physical models that can be mounted in other types of configurations.

In some embodiments, a physical tooth model can be designed virtually, and subsequently manufactured, for example by CNC machining/milling methods, other material removal methods, or by rapid prototyping methods. One or both tooth models can be digitally integrated with articulator arms and a part of a hinge arrangement, so that the tooth models can be hingedly attached to one another at the hinge arrangement. In a digital environment, the integral arms can be virtually attached to a digital model of the patient's upper and/or lower arch in an orientation that corresponds to the correct spatial relationship of a reference point (e.g., a hinge axis of the patient's jaw or the sagittal plane) to the physical models. In one aspect, the present invention includes a digital model representing a structure that when fabricated and mounted in an articulator correctly represents the actual orientation of the patient's arch. In addition, the upper and lower arches can be manufactured to accurately represent the relative positions of the teeth in each arch in occlusion, e.g., an occlusal spatial relationship.

In addition to the systems and methods described herein, the present invention further includes devices having a coded pattern. The devices and coded patterns can be designed in a variety of ways. The device can be designed to provide sufficient spatial information for defining the position of the lower and/or upper arch of a patient in relation to a reference point on the patient, e.g., the hinge axis of a patient's jaw. In some embodiments, the device having a coded pattern can include a modified facebow that is coupled to the coded pattern. For example, facebows having a variety of configurations generally known in the art can be fabricated to include a coded pattern, as described further herein. In one embodiment, the present invention includes a device having an occlusal portion and a non-occlusal portion. The occlusal portion can include a bite plate or another structure that is structurally configured to secure the device positioned in a patient's mouth during a scanning procedure. The non-occlusal portion can include a coded pattern that can have a structure designed to facilitate aligning scanned images of the patient. In some embodiments, the occlusal portion and the non-occlusal portion can be coupled together at an angle such that the coded pattern is outwardly oriented from the patient's mouth when the bite plate is positioned between the patient's teeth. The outward orientation can be spatially arranged such that the coded pattern is presented to permit scanning of the coded pattern simultaneously when scanning at least some of the patient's teeth.

In one aspect, the present invention includes a device for use in dental scanning procedures of a patient. The device can include an occlusal portion and a non-occlusal portion, the occlusal portion comprising a bite plate for securing the device positioned in a patient's mouth during a scanning procedure and the non-occlusal portion comprising a coded pattern for aligning scanned images of the patient, the occlusal portion and the non-occlusal portion being coupled together at an angle such that the coded pattern is outwardly oriented from the patient's mouth when the bite plate is positioned between the patient's teeth, so that the coded pattern is presented to permit scanning of the coded pattern simultaneously when scanning at least some of the patient's teeth. The coded patterns of the present invention can include arrangements of structures and/or characteristics of structures that are predetermined and designed to allow for determining the location of a scan on the coded pattern when only a portion of the coded pattern is scanned. For example, a scan of only a portion of the coded pattern can be acquired, but the code of the pattern (e.g., specific widths and arrangements of bars in the pattern) includes information that allows for a practitioner to determine where on the device, and the coded pattern, the scan was taken. Without a code, the location of the scan may not be readily obtainable.

Figure 7:
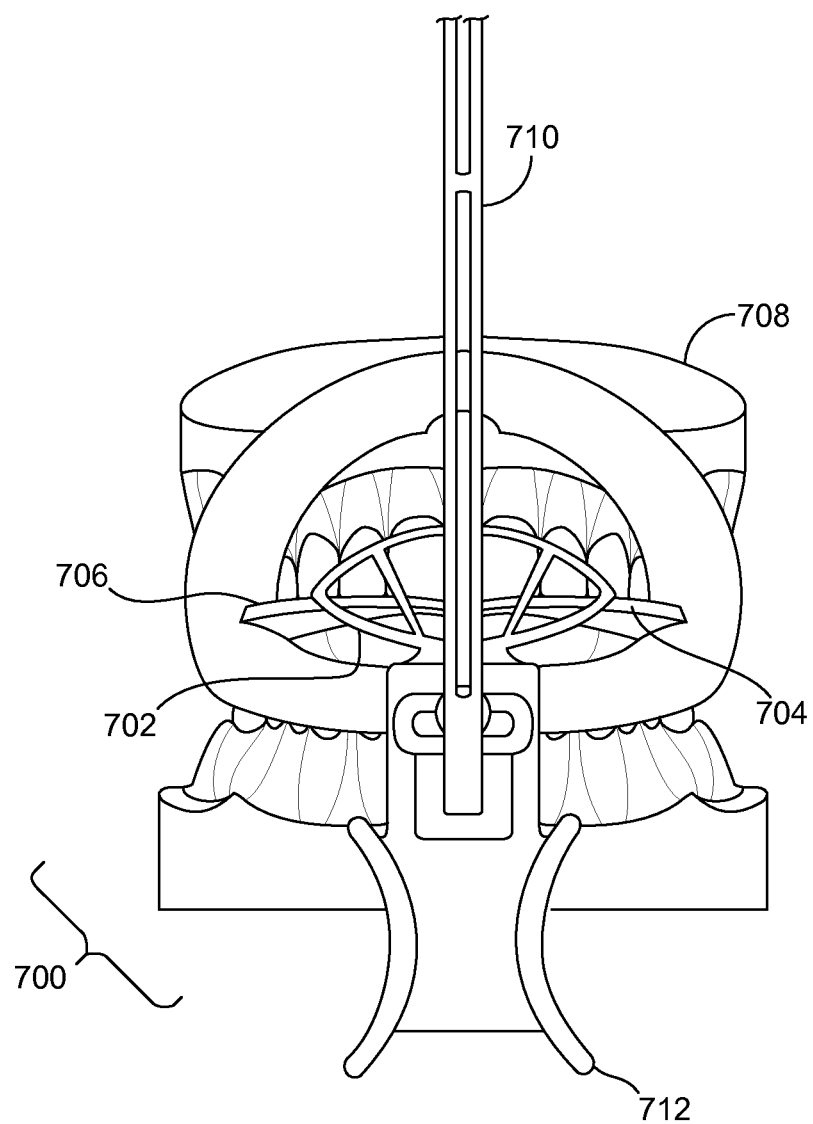
FIG. 7 shows an example device having a coded pattern in relation to teeth, in accordance with an embodiment of the present invention.

FIG. 7 shows an example of a device 700 having a coded pattern 702. As shown, the device includes an occlusal portion 704 that is placed in the patient's mouth. The occlusal portion 704, as shown, is oriented at an angle (e.g., substantially perpendicular) to the nonocclusal portion 706 that includes the coded pattern 702. As described further herein, the coded pattern 702 can have a variety of shapes and patterns. Here, the coded pattern 702 includes an oval-shaped outer ring with radiating bars oriented vertically in the outer ring. The device further includes a lip displacement attachment 708 that is integrated (e.g., molded) to the occlusal 704 and nonocclusal portions 706. In this example embodiment, the lip displacement attachment 708 includes a lip engagement feature that is shaped to move a patient's lips away from the teeth and coded pattern so as to expose at least some of the patient's teeth and allow scanning of the coded pattern in relation at least some of the patient's teeth. The device 700 of FIG. 7 also includes an extension portion 710 that can be used to align the device with a reference. For example, the extension portion 710 as shown is designed to be aligned with the sagittal plane of the patient. Additional structures can be included with the devices, e.g., FIG. 7 shows a portion of the device that provides a handle 712 for a dental practitioner or technician to hold and place the device in a patient's mouth.

Figure 8B:
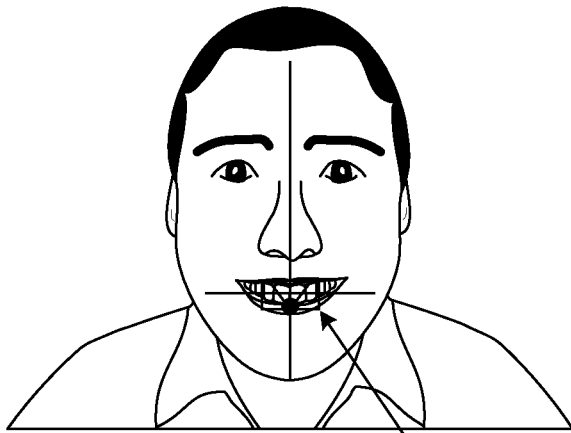
Figure 8B:

FIGS. 8A and 8B depict different views of another embodiment of a device having a coded pattern. As shown in FIG. 8A, the device can include a coded pattern having a rectangular-shaped outer ring with horizontal bars spanning the rectangle as well as vertically oriented bars intersecting the horizontal bars. In addition to the crossing horizontal and vertically-oriented bars, the coded pattern further includes an additional alignment feature (e.g., a circle) that can be used to help orient the coded pattern with a reference on the patient. For example, the additional alignment feature can be aligned with the patient's incisors. Also, the alignment feature and the coded pattern can be further integrated with several extension portions that, e.g., are oriented with a reference on the patient. For example, in FIG. 8A, the extension portions are oriented with the patient's sagittal plane as well as orthogonally to the patient's sagittal plane. As illustrated in the profile view of FIG. 8B, the device having the coded pattern can be positioned on a patient so as to also displace the patient's lips (e.g., the upper lip) so as to expose at least some of the patient's teeth and allow scanning of the coded pattern in relation at least some of the patient's teeth.

Figure 9:
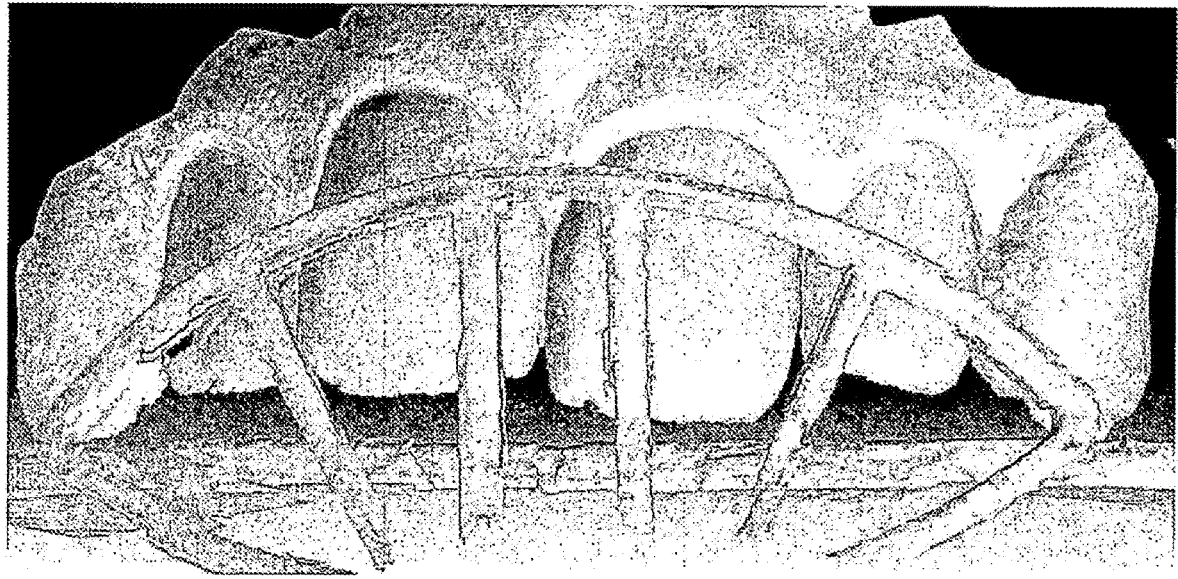
FIG. 9 provides example scan data acquired of a patient's teeth in relation to a device having a coded pattern, in accordance with an embodiment of the present invention.

As described further herein, the present invention includes scanning at least some of the patient's teeth in space with devices having coded patterns. The scan image data generated from the scanning can then be used to generate digital data showing the patient's teeth in relation to the coded pattern. FIG. 9 provides actual scan image data acquired of at least some of the patient's teeth as well as a portion of the coded pattern. It is noted that scans can include all of the coded pattern or just a portion. Furthermore, as shown here, additional scan data was acquired of the occlusal portion bite plate that is shown in the embodiment disclosed in FIG. 7.

The occlusal portion of the device can include a variety of structures. In one embodiment, the occlusal portion can be a bite plate for securing the device positioned in a patient's mouth during a scanning procedure. The bite plate can, e.g., include a material that can be used to take a bite impression of a patient, thereby making the bite plate specific for a particular patient. Alternatively, the bite plate may be standard shape that does not specifically conform to a patient's teeth. Other suitable structures for securing the device in the patient's mouth can be used.

The occlusal portion and the nonocclusal portion of the device can be coupled together. For example, the occlusal portion and the nonocclusal portion can be coupled together at an angle, such that, e.g., a planar surface of the occlusal portion is substantially orthogonal to a planar surface of the nonocclusal portion. Other angles can be used, e.g., 45 degrees or 60 degrees. In one embodiment, the occlusal portion and the non-occlusal portion can also be coupled together at an angle that is adjustable around an axis formed by the coupling of the occlusal portion and the non-occlusal portion. For example, the axis can be formed at the intersection between a planar surface of the occlusal portion and a planar surface of the nonocclusal portion.

A variety of patterns can be used for the coded patterns on the devices of the present invention. In some aspects, the coded pattern includes structures that have predetermined shapes and/or dimensions selected to allow for scanning of the coded pattern such that data from at least one scan can be used to determine the position of the scan can be determined in relation to at least the entire coded pattern, and in some embodiments the entire device. For example, the coded patterns can include varied widths, heights, shapes, sizes, orientations, markings, and/or arrangements with other structures that can be designed to allow for determination of a location in the coded pattern only if a small portion of the pattern is scanned.

In some embodiments, the coded pattern can include a plurality of bars oriented in the coded pattern at predetermined distances from each other, intersecting at predetermined angles, or both. The coded pattern can include horizontal bars intersected vertically oriented bars disposed at different angles with respect to the horizontal bars. In certain embodiments, the coded pattern can include bars oriented in a radial pattern. Furthermore, the bars of the coded pattern can be integrated with an outer structure, such as an oval, circle, square, rectangle or some other geometrical structure. The outer structure can be closed or open.

Figure 10A:
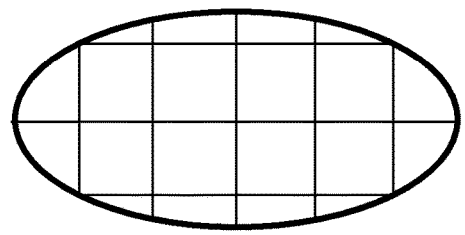
FIGS. 10A-D illustrate examples of coded patterns, in accordance with some embodiments of the present invention.
Figure 10B:
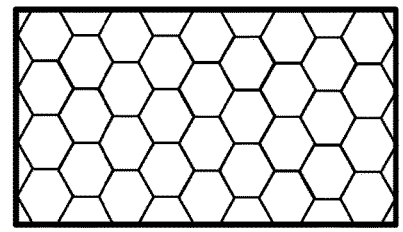
Figure 10C:
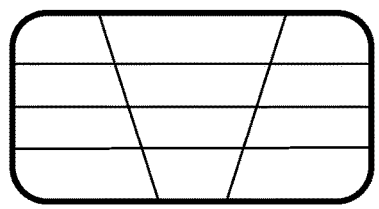
Figure 10D:
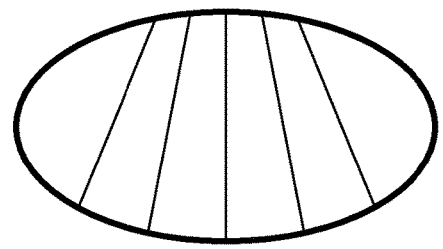

FIGS. 10A-D show just a few example coded patterns that can be used. For example, FIG. 10A shows an oval-shaped outer ring with intersecting crosshatch bars. Alternatively, FIG. 10B shows a honeycomb pattern within a rectangular outer ring. FIG. 10C depicts a patter similar to that shown in FIG. 7 in which a rounded rectangular-shaped outer ring is integrated with horizontal, parallel bars intersecting vertically oriented bars. FIG. 10D shows an oval-shaped outer ring with radially oriented bars.

Figure 11:
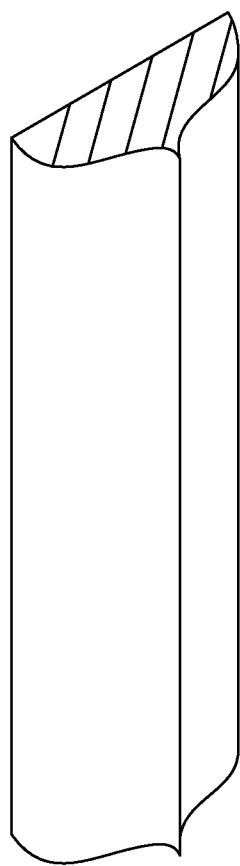
FIG. 11 shows a lengthwise portion of a coded pattern shaped to provide a reference line, in accordance with an embodiment of the present invention.

To further assist in aligning the coded pattern with structures in another image, the devices disclosed herein can further include a portion of the device that defines additional reference features for facilitating alignment. For example, a coded pattern can include a lengthwise portion forming a reference line for aligning images acquired during the scanning procedure. FIG. 11 shows an example of this embodiment. As shown, all or a portion of the coded pattern or another section of the device can be formed to have a shape that generates a ridge feature that can provide a reference line along the length of the portion of the device. In context, for example, with the coded pattern shown in FIG. 7 and the scan image data of FIG. 9, a ridged feature (not shown in FIG. 7 or 9) in the coded pattern can further add another reference feature to align two images, thereby improving ease and speed of working with the scan image data. While a straight line is shown in FIG. 11, other embodiments can be used, such as a line having predetermined curvature or bends.

It is understood that the examples and embodiments described herein are for illustrative purposes only and that various modifications or changes in light thereof may be suggested to persons skilled in the art and are included within the spirit and purview of this application and scope of the appended claims. Numerous different combinations of embodiments described herein are possible, and such combinations are considered part of the present invention. In addition, all features discussed in connection with any one embodiment herein can be readily adapted for use in other embodiments herein. The use of different terms or reference numerals for similar features in different embodiments does not necessarily imply differences other than those which may be expressly set forth. Accordingly, the present invention is intended to be described solely by reference to the appended claims, and not limited to the preferred embodiments disclosed herein.

What is claimed is:

1. A device for use in dental scanning procedures of a patient, the device comprising:
   an occlusal portion for securing the device in a mouth of the patient during an optical scan of exposed teeth of the patient; and
   a non-occlusal portion having a coded pattern integrated therein for aligning scanned 3D model data of the exposed teeth of the patient, the non-occlusal portion and the occlusal portion being arranged in order to capture the coded pattern in the scanned 3D model data of the exposed teeth when the patient's teeth are in contact with the occlusal portion.

2. The device of claim 1, wherein the scanned 3D model data is data from the optical scan, and wherein the coded pattern is arranged to be superimposed over at least a portion of the exposed teeth when an optical scan image is taken from an angle facing the patient.

3. The device of claim 1, further comprising a lip displacement attachment configured to move a lip of the patient so as to expose at least some of the patient's teeth and allow scanning of the coded pattern in relation to the at least some of the patient's teeth.

4. The device of claim 1, wherein the coded pattern comprises a plurality of bars oriented in the coded pattern at predetermined distances from each other, intersecting at predetermined angles, or both.

5. The device of claim 1, wherein the coded pattern comprises horizontal bars intersecting vertically oriented bars disposed at different angles with respect to the horizontal bars.

6. The device of claim 1, wherein the coded pattern comprises bars in a radial pattern, a crosshatch pattern, or a honeycomb pattern.

7. The device of claim 1, wherein the coded pattern comprises at least one portion that comprises a lengthwise portion forming a reference line for aligning images acquired during the scanning procedure.

8. The device of claim 1, wherein the non-occlusal portion comprises a ring structure.

9. The device of claim 1, wherein the coded pattern further comprises an alignment feature configured to facilitate orienting the coded pattern with a reference on the patient.

10. The device of claim 9, wherein the reference comprises one or more teeth of the patient.

11. The device of claim 1, wherein the occlusal portion is coupled to the non-occlusal portion.

12. The device of claim 11, wherein the occlusal portion is coupled to the non-occlusal portion at an adjustable angle.

13. The device of claim 11, wherein one or both of the occlusal and non-occlusal portions comprise planar surfaces.

14. A system for digitally aligning a patient's teeth with a reference portion of the patient, the system comprising:
   a device comprising:
      an occlusal portion for securing the device in a mouth of the patient during an optical scan of exposed teeth of the patient; and
      a non-occlusal portion separate from the occlusal portion, the non-occlusal portion having a coded pattern integrated therein for aligning scanned 3D model data of the exposed teeth of the patient, the non-occlusal portion and the occlusal portion being arranged in order to capture the coded pattern in the scanned 3D model data of the exposed teeth;
   a scanner for acquiring a first image of at least a portion of the patient's teeth and a second image of the coded pattern and the at least the portion of the patient's teeth; and
   a computer comprising storage media comprising instructions that, when executed, cause the computer to determine a spatial relationship between at least some of the patient's teeth and the reference portion associated with the patient by calculating a first spatial relationship between the device and the at least the portion of the patient's teeth and a second spatial relationship between the device and the reference portion.

15. The system of claim 14, further comprising a lip displacement attachment configured to move a lip of the patient so as to expose the at least some of the patient's teeth and allow scanning of the coded pattern in relation to the at least some of the patient's teeth.

16. The system of claim 14, wherein the coded pattern comprises a plurality of bars oriented in the coded pattern at predetermined distances from each other, intersecting at predetermined angles, or both.

17. The system of claim 14, wherein the coded pattern comprises at least one portion that comprises a lengthwise portion forming a reference line for aligning images acquired during a scanning procedure.

18. The system of claim 14, wherein the reference portion comprises a sagittal plane of the patient, a plane orthogonal to the sagittal plane, or both.

19. The system of claim 14, wherein the scanner is an optical scanner.

20. The system of claim 19, wherein the optical scanner comprises confocal optics.

* * * * *